(12) United States Patent
Wagener et al.

(10) Patent No.: US 6,605,748 B2
(45) Date of Patent: Aug. 12, 2003

(54) REACTION MIXTURES FOR METATHESIS

(75) Inventors: Kenneth Wagener, Gainesville, FL (US); James Pawlow, Canton, OH (US); John Sworen, Gainesville, FL (US)

(73) Assignee: University of Florida

( * ) Notice: Subject to any disclaimer, the term of this patent is extended or adjusted under 35 U.S.C. 154(b) by 0 days.

(21) Appl. No.: 10/227,127

(22) Filed: Aug. 23, 2002

(65) Prior Publication Data

US 2003/0092928 A1 May 15, 2003

Related U.S. Application Data

(62) Division of application No. 09/849,100, filed on May 4, 2001, now Pat. No. 6,521,779.
(60) Provisional application No. 60/201,918, filed on May 4, 2000.

(51) Int. Cl.[7] ............................................... C07C 33/03
(52) U.S. Cl. ...................................... 568/852; 556/136
(58) Field of Search .......................... 568/852; 556/136

(56) References Cited

U.S. PATENT DOCUMENTS 6,111,149 A * 8/2000 Schwab et al. ............. 568/904
6,156,692 A * 12/2000 Nubel et al. ................ 502/155
6,159,890 A * 12/2000 Nubel et al. ................ 502/155
6,215,019 B1 * 4/2001 Pederson et al. ........... 560/234

* cited by examiner

Primary Examiner—Joseph K. McKane
Assistant Examiner—Kamal Saeed
(74) Attorney, Agent, or Firm—Akerman Senterfitt; Stanley A. Kim

(57) ABSTRACT

Functionalized allylic olefins are condensed by metathesis using the catalyst 1,3-dimesityl-4,5-dihydroimidazol-2-ylidene ruthenium benzylidene [Ru*].

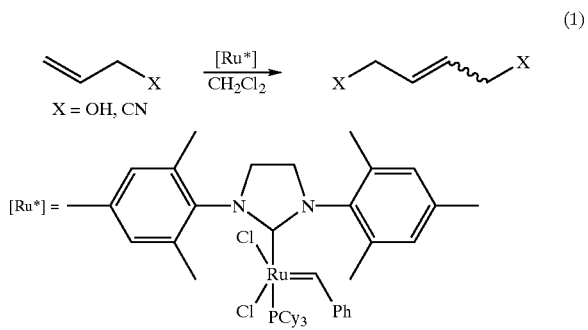

7 Claims, 1 Drawing Sheet

(1) =

Mes = $C_6H_2$-2,4,6-$(CH_3)_3$

METATHESIS          HYDROGENATION

X = Functional Group

REACTION MIXTURES FOR METATHESIS

CROSS REFERENCE TO RELATED APPLICATION

The present application is a division of U.S. patent application Ser. No. 09/849,100 now U.S. Pat. No. 6,521,799 filed May 4, 2001 entitled "Metathesis of Functionalized Allylic Olefins," which claims the benefit of U.S. Provisional patent application No. 60/201,918 filed May 4, 2000 and entitled "Metathesis Dimerization of Functionalized Allylic Olefins."

STATEMENT AS TO FEDERALLY SPONSORED RESEARCH

This invention was made with United States Government support awarded by the Army Research Office, Grant No. DAAG55-97-1-0023; and by the National Science Foundation, Division of Materials Research, Grant No. DMR-9806492. The United States Government has certain rights in this invention.

FIELD OF THE INVENTION

The invention relates generally to the field of polymer chemistry. More particularly, the invention relates to metathesis of functionalized allylic olefins.

BACKGROUND

Olefin metathesis is a reaction commonly employed in polymer chemistry. In this reaction, the carbon-carbon double bonds present in a starting olefin molecule (substrate) are broken, and the molecule is rearranged into a new olefin molecule (product). Several varieties of olefin metathesis are known including acyclic diene metathesis (ADMET), ring-opening metathesis polymerization (ROMP), and ring-closing metathesis polymerization (RCM). The basic mechanism for each of these processes is thought to involve a cycloaddition reaction between the starting olefin molecule and a transition metal alkylidene complex that causes the formation of an intermediate metallacyclobutane. The intermediate metallacyclobutane breaks up to form the new olefin molecule and a new alkylidene.

Several generations of catalysts have been developed for olefin metathesis reactions. Among these, so-called "Black Box" catalysts consist of a high valent transition metal halide (or oxide or halo-oxide) together with an alkylating component such as alkyl aluminum or alkyl zinc. Other metathesis cataylsts include: titanocene-based catalysts; Schrock's tungsten (W), molybdenum (Mo), and rhenium (Re) catalysts; and Grubbs' ruthenium (Ru) catalysts (e.g., compound (1) shown below).

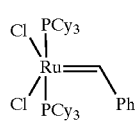

(1)

Each of the foregoing catalysts has certain advantages and disadvantages that make each more suited for some applications, but less suited for others. For example, Black Box catalysts are known to have a very low tolerance for functional groups, while Schrock's catalysts have a higher tolerance for functional groups but are sensitive to air and moisture.

Although catalysts such as Schrock's and Grubbs' catalysts have been shown to exhibit tolerance for functional groups, even these have only limited catalytic activity in some reactions. For example, the foregoing catalysts show poor activity when olefins containing electron-rich functionalitie's are employed as substrates. Moreover, metathesis activity is substantially decreased or inhibited when a heteroatom is placed near the olefin site. See, e.g., Furstner, A., ed. In *Alkene Metathesis in Organic Synthesis*. Springer-Verlag: Berlin, 1998; Ivin and Mol, In *Olefin Metathesis and Metathesis Polymerization*, 2nd ed.; Academic: San Diego, 1997. Presumably, an alkylidene chelate complex (3) is formed between the metal and the olefin (2), deactivating the catalyst as shown below ($L_n$=an organic ligand; Ph=phenyl).

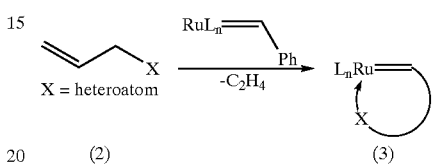

(2)     (3)

This effect is most pronounced with respect to vinyl and allylic olefins. For example, Hoye has shown that RCM of allylic alcohols using Grubbs' ruthenium catalyst (1) can require up to 1 equivalent of catalyst to efficiently promote the metathesis reaction. Hoye and Zhao, *Org. Lett.* 1999, 1, 1123. In addition, in some cases, these molecules are metathesis inactive when using either Grubbs' ruthenium catalyst (1) or Schrock's molybdenum catalyst. See, Schwab, et al., *Angew. Chem. Int. Ed. Engl.* 1995, 34, 2039; Schwab et al., *J. Am. Chem. Soc.* 1996, 118, 100; and Belderrain and Grubbs, *Organometallics* 1997, 16, 4001; Bazan et al., *J. Am. Chem. Soc.* 1991, 113, 6899; Bazan et al., *J. Am. Chem. Soc.* 1990, 112, 8378; Schrock et al., *J. Am. Chem. Soc.* 1990, 112, 3875; Schrock, R. R. *Tetrahedron* 1999, 55, 8141; and Schrock, R. R. *Polyhedron* 1995, 14, 3177).

These limitations of conventional olefin metathesis chemistry result in increased costs of several industrially useful feedstock chemicals such as functionalized monomers used to produce various polymers. Therefore, because the cost of allylic olefins is less than of alkenes containing distant functional groups, a metathesis-based method for producing such feedstock chemicals from allylic olefins is expected to reduce the overall costs of producing certain polymers. For example, a metathesis-based method of making 1,4-butanediol from allyl alcohol could reduce the costs of producing polybutylene terephthalate (PBT). Similarly, the ability to successfully condense other functionalized allyl olefins (e.g., allyl cyanide) would be useful to produce feedstock chemicals that could be used in the production of other polymers such as nylon 6,6.

SUMMARY

The invention relates to the discovery of an improved method for making functionalized allylic olefins useful in the production of industrially important polymers. The method utilizes 1,3-dimesityl-4,5-dihydroimidazol-2-ylidene ruthenium benzylidene [Ru*] (4), the ruthenium-based metathesis catalyst shown below (Cy=cyclopentyl) that was recently developed by Grubbs and coworkers using imidazolium ligands. See, Scholl et al., *Org. Lett.* 1999, 1:953.

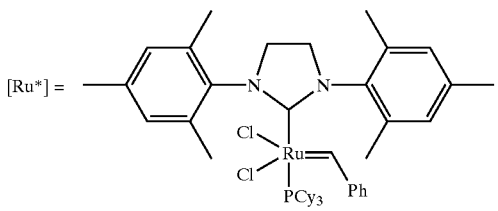

Using this catalyst, it has been shown for the first time that functionalized olefins such as allyl alcohol and allyl cyanide are efficiently and effectively converted to new olefin products by metathesis condensation. Consequently, the present invention should facilitate the synthesis of a broad range of molecules not previously producible via metathesis chemistry.

Accordingly, the invention features a method for condensing a functionalized allylic olefin substrate by metathesis chemistry. The method includes the steps of: (a) providing a functionalized allylic olefin substrate; (b) providing a ruthenium-based catalyst capable of catalyzing the metathesis condensation of the functionalized allylic olefin substrate; (c) contacting the functionalized allylic olefin substrate with the catalyst to form a reaction mixture; and (d) placing the reaction mixture under conditions that result in the formation of a functionalized olefin product via metathesis condensation, the functionalized olefin product having a different chemical structure than the functionalized allylic olefin substrate.

The catalyst used in this method can be 1,3-dimesityl-4,5-dihydroimidazol-2-ylidene ruthenium benzylidene (Ru*). The functionalized allylic olefin substrate can be functionalized with an electron rich functional group. For example, the functionalized allylic olefin substrate can be allyl alcohol or allyl cyanide. Where the functionalized allylic olefin substrate is allyl alcohol, the functionalized allylic olefin product can be 2-butene-1,4-diol. Where the functionalized allylic olefin substrate is allyl cyanide, the functionalized allylic olefin product can be 1,4-dicyanobutene.

The step of placing the reaction mixture under conditions that result in the formation of the functionalized olefin product via metathesis condensation can include placing the reaction mixture at a temperature of between about 10° C. and 70° C.; placing the reaction mixture at a temperature of about 23° C. or less; placing the reaction mixture under about standard atmospheric pressure; applying a vacuum force to the reaction mixture; and/or placing the reaction mixture under an inert atmosphere (e.g., under $N_2$ or Ar). This step can also be performed under anhydrous conditions. The substrate:catalyst ratio (mol:mol) used in this method can be between about 1:1 to 1000:1, and is preferably greater than about 10:1.

The method of the invention can further include a step (e) of hydrogenating the functionalized allylic olefin product. This hydrogenation step can be catalyzed using residue of the ruthenium-based catalyst formed during the step of placing the reaction mixture under conditions that result in the formation of a functionalized olefin product via metathesis condensation. In this aspect of the method of the invention, where the functionalized allylic olefin substrate is allyl alcohol and the functionalized allylic olefin product is 2-butene-1,4-diol, the step of hydrogenating the functionalized allylic olefin product can result in the production of butane-1,4-diol.

The invention also features a reaction mixture including a functionalized allylic olefin substrate; a ruthenium-based catalyst capable of catalyzing the metathesis condensation of the functionalized allylic olefin substrate; and a solvent, the solvent having dissolved therein the substrate and the catalyst. In this reaction mixture, the catalyst can be 1,3-dimesityl-4,5-dihydroimidazol-2-ylidene ruthenium benzylidene (Ru*); the functionalized allylic olefin substrate can be allyl alcohol and allyl cyanide; and the solvent can be a hydrocarbon-based solvent such as dichloromethane, tetrahydrofuran, dimethoxyethane, or acetone.

Another reaction mixture within the invention includes a functionalized allylic olefin substrate; a ruthenium-based catalyst capable of catalyzing the metathesis condensation of the functionalized allylic olefin substrate; a functionalized olefin product having a different chemical structure than the functionalized allylic olefin substrate, the product being formed by the metathesis condensation of the substrate; and a solvent, the solvent having dissolved therein the substrate and the catalyst. In this reaction mixture, the catalyst can be 1,3-dimesityl-4,5-dihydroimidazol-2-ylidene ruthenium benzylidene (Ru*); and the functionalized allylic olefin substrate can be allyl alcohol or allyl cyanide. Where the functionalized allylic olefin substrate is allyl alcohol, the functionalized allylic olefin product can be 2-butene-1,4-diol. And where the functionalized allylic olefin substrate is allyl cyanide, the functionalized allylic olefin product can be 1,4-dicyanobutene.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including any definitions will control. In addition, the particular embodiments discussed below are illustrative only and not intended to be limiting.

Other features and advantages of the invention will be apparent from the following detailed description, and from the claims.

BRIEF DESCRIPTION OF THE DRAWINGS

The above and further advantages of this invention may be better understood by referring to the following description taken in conjunction with the accompanying drawings, in which.

DETAILED DESCRIPTION

Figure 1:
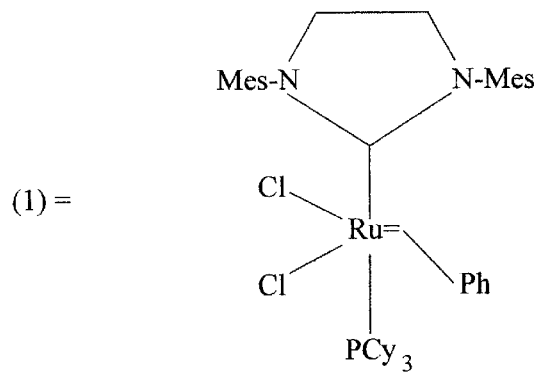
FIG. 1 is a schematic description of (a) the metathesis condensation of a functionalized allylic olefin to form a new olefin product, and (b) the hydrogenation of the product.
Figure 1:
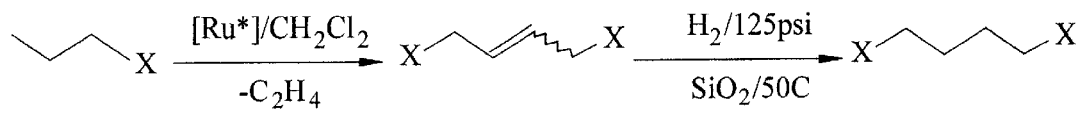

The invention is based on the discovery of a new method for catalyzing the metathesis condensation of functionalized olefins. A preferred reaction of the invention is the condensation of allylic olefins by metathesis chemistry using the catalyst Ru*. Referring to FIG. 1 an overview of an illustrative reaction is presented wherein an allylic olefin substrate having a functional group X is mixed with the Ru* catalyst in various substrate:catalyst ratios in a solvent such as dry dichloromethane. The reaction is allowed to proceed under conditions (e.g., with stirring under inert atmosphere at 35° C. overnight) that result in the production of a new olefin product via metathesis condensation. During this reaction, ethylene is released as the new olefin product is produced.

After the metathesis step, an optional hydrogenation step can be performed wherein the catalyst residue is absorbed onto silica gel and reaction mixture is pressurized under a hydrogen atmosphere. The absorbed ruthenium catalyst is modified by reaction with the silica gel to produce a heterogenous active hydrogenation catalyst. Upon hydrogenation, the metathesis product (e.g., 2-butene-1,4-diol) is converted to its desired product (e.g., butane-1,4-diol).

While the foregoing describes one particularly preferred version of the invention, many other methods and compositions are also within the scope of the invention. Examples of these are described below in further detail.

General Methods

The invention utilizes general techniques known in the field of polymer chemistry. General polymer chemistry concepts and methods relating to the invention are described in *Polymer Handbook* (4$^{th}$ Edition), eds., Brandup et al., New York, John Wiley and Sons, 1999; and *Polymer Synthesis and Characterization: A Laboratory Manual*, eds. Sandler et al., Academic Press, 1998. Concepts and methods relating more specifically to metathesis chemistry are described in *Alkene Metathesis in Organic Synthesis*. Springer-Verlag: Berlin, 1998 and *Olefin Metathesis and Metathesis Polymerization*, 2nd ed.; Academic: San Diego, 1997.

Substrates

In methods within the invention, an olefin molecule is used as a substrate that is converted into a new olefin molecule by metathesis reaction. Any type of olefin molecule capable of being converted into a new olefin molecule by the metathesis method taught herein may be used a substrate. Since the methods of the invention overcome previous impediments in the metathesis condensation of functionalized olefins, such molecules are preferred for use as substrates. In the examples described below, functionalized allylic olefins such as allyl alcohol and allyl cyanide are used as substrates. Nonetheless, based on the teachings provided herein, it is expected that allylic olefins functionalized with other groups (e.g., silane, stannane, aldehydes, carboxylic acid, etc.) would serve as suitable substrates as well. Preferred conditions for condensing such other functionalized allylic olefins can be identified by performing the reaction described for allyl alcohol and allyl cyanide under various reaction conditions to identify those under which a particular reaction proceeds efficiently. The conditions described herein can be used as a general guide in setting the ranges of the reaction conditions to be tested. In the experiments described below, standard ACS reagent grade chemicals were used as substrates and are available from Aldrich (St. Louis, Mo.) or Fisher Scientific (Hampton, N.H.). Allylic olefins with functional groups other than —OH and —CN are also available from these suppliers.

Catalysts

The metathesis reaction of an olefin according to the invention is facilitated using a catalyst. Any catalyst compatible with the methods of the invention may be used. However, because of the resistance to functional groups and efficiency of catalysis, Ru-based catalysts that exhibit such functionality resistance are preferred. For example, Ru* is particularly preferred because of its ability to efficiently catalyze the metathesis of allyl alcohol and allyl cyanide. A number of other catalysts might be employed in the reaction was well. The suitability of such catalysts for a particular reaction within the invention can be determined by substituting the catalyst for Ru* in the reaction, and then assessing the efficiency of catalysis in the reaction (e.g., by measuring the amount of product formed). For instance, based on the data presented herein, it is thought that Ru-based catalysts having a structure similar to Ru* might be used in the invention.

Such structurally similar catalysts are known. These include well-defined Ru-alkylidene complexes bearing N-heterocyclic carbene ligands (e.g., those bearing phosphane or imidazolylidene ligands) and ruthenium vinylidene complexes bearing N-heterocyclic carbene ligands. See, Louie and Grubbs, *Agnew. Chem. Int. Ed.* 2001, 40:247; and Trnka and Grubbs, *Acc. Chem. Res.*, 200 1, 34:18. For example, Bielawski et al., *Polymer*, 2001, 42:4939 describes 1,3-bis (2,4,6-trimethylphenyl)imidazol-2-ylidene and structurally similar compounds that might be used as the catalyst in some reactions within the invention. Other structurally similar catalysts are described in international patent application WO 00/43343 published Jul. 27, 2000. U.S. Pat. No. 6,048,993 also describes Ru-based catalysts with some similarity to Ru* that might be used in the invention. Exemplary catalysts described therin have the following general formula:

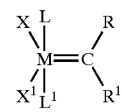

wherein M is ruthenium or osmium; X and X$^1$ are independently any anionic ligand; L and L$^1$ are any neutral electron donor ligand; and, R and R$^1$ are each hydrogen or one of the following substituent groups: C$_2$–C$_{20}$ alkenyl, C$_2$–C$_{20}$ alkynyl, C$_1$–C$_{20}$ alkyl, aryl, C$_1$–C$_{20}$ carboxylate, C$_1$–alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkyl C$_1$–C$_{20}$ alkylsulfonyl and C$_1$–C$_{20}$ alkylsulfinyl.

By varying the catalyst employed for a particular metathesis reaction within the invention, it may be possible to increase product yields and reduce reaction times. For example, if a catalyst exhibiting greater thermal stability than Ru* is selected, it may be possible to increase the reaction rate by increasing the temperature of the reaction mixture without the catalyst decomposing. Other reaction conditions, such as choice of solvent (e.g., solvent with higher boiling points might be used) might be varied as well. Based on the teaching herein, suitable catalysts for particular metathesis condensation reactions can be determined by examining the catalytic activity of a number of different catalysts in the particular reaction, and selecting as suitable those displaying any catalytic activity. Those particular catalysts that display higher levels of activity are preferred, and those that display the highest levels of activity are more preferred.

Solvents

One or more solvents can be added to the reaction mixture to help dissolve the substrate and catalyst of the reaction mixture into a homogeneous state (e.g., substrate and catalyst dissolved together in a liquid phase). Those solvents capable of both dissolving the constituents of the process and not significantly hindering the reaction are acceptable for use with the invention. Typically, the choice of the solvent depends upon the particular constituents used, as, for example, one particular solvent may be capable of dissolving one set of constituents but not another. As such, many types of solvents can be used with this process. A non-exhaustive list of examples of solvents that might be used include various hydrocarbon-based solvents such as aliphatic hydrocarbons (e.g., hexane and heptane), aromatic hydrocarbons (e.g., benzene, toluene, naphthalene, phenol, and aniline), alicyclic and heterocyclic hydrocarbons (e.g., cyclohexane), cyclic ethers, and derivatives of any of the foregoing (e.g., halogenated derivatives of the foregoing such as chloroform and dichloromethane). In the experiments presented below, dichloromethane, benzene, tetrahydrofuran (THF), dimethoxyethane (DME), and acetone were used as solvents. Mixtures of two or more solvents might also be used. The suitability of a particular solvent for a particular reaction can be determined empirically by the methods taught herein. For example, a given solvent can be selected for a particular reaction based on the ability of the solvent to dissolve the constituents of the reaction and the boiling point of the solvent (which should be above the temperature of the reaction). A candidate solvent can be used in the reaction to determine whether it is suitable.

For the metathesis condensation of allyl alcohol, solvents that allowed the reaction to occur include dichloromethane and THF. Dichloromethane also allowed the metathesis of allyl cyanide to proceed. In some cases, the use of an anhydrous solvent is preferred to prevent the formation of unwanted by-products of the reaction. In addition, the use of chlorinated solvents over non-chlorinated solvents is sometimes preferred to increase yield of the desired olefin product while decreasing the yield of undesired by-products of the reaction.

The amount of solvent used in a particular application of the invention will vary depending on the particular substrate, catalyst, and reaction conditions employed. The amount of solvent used should be in excess of the amount needed to (a) dissolve the substrate and catalyst under the reaction conditions selected and (b) allow that reaction to proceed. Based on the results obtained below, 1 ml of solvent for up to about 300 mg of substrate/catalyst mixture is a sufficient amount. For other applications, a solvent to substrate-catalyst ratio of between about 1 ml:0.1 to 1000 mg is expected to be an appropriate ratio for carrying out the reaction.

Substrate:Catalyst Ratios

The efficiency of the subject metathesis condensation can be adjusted by varying the amount of substrate per amount of catalyst used in the reaction. The substrate:catalyst ratio used in the invention can be any that result in the formation of the desired olefin product. This ratio will vary widely depending on factors such as the particular catalyst selected, the particular reaction to be catalyzed, the quantity or concentration of substrate present, the solvent selected, and the particular reaction conditions (e.g., pressure, temperature, etc.) utilized. Such substrate:catalyst ratios can be determined empirically by comparing the amount of desired product produced using a range of different ratios. Those that produce more of the product are typically preferred; and those that produce the most product are typically the most preferred. In general, for the metathesis condensation of a functionalized allylic olefin, the ratio of substrate to catalyst (mol:mol) can be varied from about 1:1 to 1000:1 (e.g., 0.9:1, 1:1, 2:1, 3:1, 4:1, 5:1, 10:1, 20:1, 30:1, 40:1, 50:1, 75:1 , 100:1, 150:, 200:1, 300:1, 400:1, 500:1, 750:1, 1000:1, and 1100:1). Too much catalyst might be disadvantageous from an economic standpoint (catalysts generally being relatively expensive), while too little catalyst might be disadvantageous from an efficiency standpoint (i.e., too little product results). Accordingly, a preferred substrate:catalyst ratio is also one that produces the most economically efficient reaction.

As one example, for the metathesis condensation of allyl alcohol using dichloromethane as a solvent at 40° C., suitable substrate:catalyst ratios include 42:1, 60:1, 101:1, 111:1, and 380:1. Using THF as a solvent at 23° C. or 60° C., a substrate:catalyst ratio of 110:1 resulted in the production of olefin product. As another example, for the metathesis condensation of allyl cyanide using dichloromethane as a solvent at 40° C., suitable substrate:catalyst ratios include 10:1, 25:1, 50:1, 57:1, 100:1, and 250:1.

Reaction Conditions

A variety of different reaction conditions will result in the metathesis condensation of an olefin. The particular conditions to be employed will vary depending on the particular olefin substrate used, the particular catalyst used, the substrate:catalyst ratio used, and the solvent in which the reaction takes place. Suitable conditions are described below. Other suitable conditions, however, are within the invention and can be determined empirically using the information provided below.

Temperature

Methods within the invention include a step of placing the substrate/catalyst/solvent mixture under conditions that result in the production of the olefin product in the reaction mixture. This step typically (but not always, as the reaction can proceed at room temperature in many cases) includes adjusting the temperature of the reaction mixture to a temperature suitable for the reaction to proceed. The particular temperature or range of temperatures chosen will vary according to several parameters including the particular reaction selected, the concentration of the reactants in the reaction mixture, the pressure of the reaction mixture, etc. Suitable temperatures can be determined by extrapolation from temperatures known to be optimal for reactions similar to those of the selected reaction (i.e., from conventional metathesis methods or from similar methods using conventional catalysts) to get a general range of suitable temperatures. Experiments can then be performed using a catalyst described herein in an adaptation of the conventional methods, and the temperature can be varied around the extrapolated general range of suitable temperatures to identify suitable and/or optimal temperature(s) for the processes of the invention.

Generally, those temperatures at which the greatest amount of chemical product is produced are preferred. In some cases, those temperatures which do not necessarily result in the greatest amount of chemical product are preferred for other reasons (e.g., from an economic standpoint it may be preferred to run the reaction at lower temperatures to avoid the costs associated with heating a reaction mixture or to avoid decomposition of expensive catalysts). For many reactions, suitable temperatures range from about 10° C. to about 70° C. (e.g., 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, and 72° C.), although this range can vary substantially.

For the metathesis condensation of allylic alcohol using the Ru* catalyst, reaction conditions including reaction temperatures ranging from about room temperature (e.g., 23° C.) to 60° C. have resulted in the production of olefin product. For the metathesis condensation of allylic cyanide using the Ru* catalyst, reaction temperatures ranging from about 40 to 50° C. have resulted in the production of olefin product. Reactions run at temperatures colder than about 23° C. are expected to produce olefin product as well, but at increasingly slower rates as the temperature is reduced (the reaction kinetics slowing with decreasing temperature). Reactions run at temperatures hotter than about 60–70° C. might also produce olefin product. In many cases, the product yield will decrease as the temperature increases due to the decomposition of thermally labile catalysts or substrates. In general, the maximum temperature at which the reaction can proceed is expected to be limited by the stability of the catalyst used under the specific reaction conditions employed.

Atmosphere

The reaction of the invention can be performed under any atmosphere that allows the reaction to proceed. For catalysts such as Ru* that lose activity in the presence of oxygen, a deoxygenated, inert atmosphere such as nitrogen ($N_2$) or argon is preferred. For catalysts that lose activity in the presence of water, a dry atmosphere is preferred. For the metathesis condensation of allylic olefins using the Ru* catalyst, the reaction is preferably performed under an inert gas such as argon.

Pressure

Although the substrate/catalyst/solvent mixture according to the invention can react under standard atmospheric pressure to result in the production of the olefin product, methods within the invention might also include a step of adjusting the pressure of the reaction mixture to another pressure at which the reaction can proceed. The particular pressure or range of pressures chosen will vary according to several parameters including the particular reaction selected, the concentration of the components in the reaction mixture, the temperature of the reaction mixture, etc. Suitable pressures can be determined by extrapolation from pressures known to be optimal for reactions similar to those of the selected reaction (i.e., from conventional metathesis methods or from methods using a similar combination of reaction components) to obtain a general range of suitable pressures. Experiments can then be performed by using a reaction mixture of the invention in an adaptation of the conventional methods, and the pressure can be varied around the extrapolated general range of suitable pressures to find the most optimal pressure(s) for the processes of the invention. For example, those pressures at which the greatest amount of desired olefin product is produced might be optimal. Although metathesis condensation of an olefin can take place at pressures greater than atmospheric pressure, it is generally preferred to run the reaction at about standard atmospheric pressure (because no specialized containment is necessary) or less. Where a volatile product is produced, it may be preferred to run the reaction at less than standard atmospheric pressure (e.g., in vacuo or at about 10, 25, 50, 100, 200, 300, 400, 500, 600, 700, 800, or 900 kPa), as removal of the evolved volatile product (e.g., ethylene) is expected to drive the reaction forward (to the right as shown herein) at a higher rate.

Duration

The duration of the reaction will depend upon the particular reaction and reaction conditions selected. Generally, the amount of time for the reaction to occur will vary from the time between (a) the initiation of the reaction and the first appearance of the desired chemical product and (b) the initiation of the reaction and the termination of chemical product synthesis (e.g., due to exhaustion of substrate or production of interfering by-products). Thus the reaction can last for less than a few seconds to more than several days. The reaction can even proceed continuously by continuous removal of desired product and by-products, and continuous replenishment of substrate, catalyst, take place at pressures greater than atmospheric pressure, it is generally preferred to run the reaction at about standard atmospheric pressure (because no specialized containment is necessary) or less. Where a volatile product is produced, it may be preferred to run the reaction at less than standard atmospheric pressure (e.g., in vacuo or at about 10, 25, 50, 100, 200, 300, 400, 500, 600, 700, 800, or 900 kPa), as removal of the evolved volatile product (e.g., ethylene) is expected to drive the reaction forward (to the right as shown herein) at a higher rate.

Duration

The duration of the reaction will depend upon the particular reaction and reaction conditions selected. Generally, the amount of time for the reaction to occur will vary from the time between (a) the initiation of the reaction and the first appearance of the desired chemical product and (b) the initiation of the reaction and the termination of chemical product synthesis (e.g., due to exhaustion of substrate or production of interfering by-products). Thus the reaction can last for less than a few seconds to more than several days. The reaction can even proceed continuously by continuous removal of desired product and by-products, and continuous replenishment of substrate, catalyst, and/or solvent. For the metathesis condensation of allyl alcohol or allyl cyanide under the reaction conditions described below, the reaction generally lasts from 1–24 hours (e.g., 1, 2, 5, 12, 18, or 24 hours; see examples below).

Isolation/Purification and Further Processing of Products

The chemical products resulting from a reaction according to the invention can be isolated from the reaction mixture by any suitable means, e.g., filtration, chromatography, distillation, etc. The isolated products can be further purified by conventional methods as well.

The products produced according to the invention can be further processed according to standard methods. For example, the olefin products of the metathesis condensation of allyl alcohol and allyl cyanide can be hydrogenated using Ru catalyst residue (e.g., from the metathesis condensation reaction) over silica gel in the presence of high pressure hydrogen gas (see, Watson and Wagner, *Macromolecules* 33:8963, 2000) to respectively produce 1,4-butanediol and 1,4-dicyanobutane, compounds useful in the production of polyesters and polyamides. See, Crabtree, R. H. *The Organometallic Chemistry of the Transition Metals*, 2nd Ed., Wiley: New York, 1994; and Odian, G. *Principles of Polymerization*, 3rd Ed., Wiley: New York, 1991.

EXAMPLES

Example 1

General Procedure for Methatesis Condensation

Except as otherwise noted the experiments described in the below examples were performed according to the following protocol. All non-halogenated solvents were dried from Na/benzophenone ketal and the halogenated solvents were dried using CaH$_2$. All solvents were distilled into a schlenk flask and degassed before use. The monomers, allyl alcohol and allyl cyanide, were dried using CaH$_2$ during distillation.

In a dry box, the indicated amount of catalyst was placed in a 10 ml round bottom flask and capped with a reflux condenser. The dry box contained an inert atmosphere (Ar) and was free from moisture. The glassware was taken out of the box and placed on an argon purge. The argon purge used a hose containing a needle to put positive argon pressure in the round bottom flask, which was then released through a bubbler. The bubbler contained silicon oil that did not allow any air to enter the system. One ml of the indicated solvent (e.g., C$_6$H$_6$, THF or CH$_2$Cl$_2$) was added to the flask under the argon purge using a syringe. The round bottom flask was then placed in an oil bath to bring the added solvent to the required temperature for the condensation reaction. When the reaction was run at room temperature, no oil bath was used. Once the solvent reached the desired temperature, the indicated amount of substrate (e.g., allyl alcohol or allyl cyanide) was syringed into the round bottom flask. The reaction was run for the indicated time and then stopped by exposing the flask to the atmosphere. The resulting mixture was then analyzed for amount of product and by-product produced as indicated (e.g., by $^1$H NMR analysis).

EXAMPLE 2

Metathesis Condensation of Allyl Alcohol and Allyl Cyanide

Ru* was used to catalyze the metathesis condensation of allyl alcohol and allyl cyanide under a variety of reaction conditions according to the general procedure described in Example 1. The reaction is illustrated below:

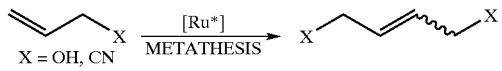

Referring to Table 1 below, Ru* catalyzed both the conversion of allyl alcohol to 2-butene-1,4-diol and the conversion allyl cyanide to 1,4-dicyanobutene. Under the conditions examined, the conversion of allyl alcohol to 2-butene-1,4-diol was more efficient than the conversion allyl cyanide to 1,4-dicyanobutene. During the reactions, evolution of ethylene occured immediately upon exposure of the olefin substrate to the Ru* catalyst. The reaction mixture solution continued to bubble for approximately 60 minutes, during which time the solution changed color from pinkish-red to golden-yellow. As the molar ratio of catalyst was increased, a corresponding increase in product yield was observed, maximizing at 10% catalyst employed (for allyl cyanide), the maximum used in this study. The by-product propionaldehyde was observed in all reactions using allyl alcohol. This by-product was most likely formed via a Ru-mediated rearrangement of the olefin from a Ru—H intermediate formed in the presence of proton source (R—OH or trace moisture). Supporting this, in other experiments, performance of the reaction under very wet conditions resulted in the production of higher quantities of propionaldehyde (and less of the desired diol product) than those performed under less wet or anhydrous conditions.

While allyl alcohol conversions were high, product yields for allyl cyanide metathesis were comparatively low. For example, at low catalyst loadings (less than 1%), no detectable metathesis product of allyl cyanide was observed whatsoever. In the experiment shown in Table 1, the optimum yield (28%) of 1,4-dicyano-2-butene was attained using a 10:1 ratio of substrate to catalyst. For the allyl cyanide experiments, at all catalyst loadings, the CH$_2$Cl$_2$ solution became dark brown within 90 minutes after the substrate was added, implying that catalyst decomposition was occurring.

TABLE 1

Metathesis Results of Allylic Olefins Using Variable Catalyst Ratios

| Olefin | Substrate:<br>Catalyst Ratio | %<br>Propionaldehyde | % Condensation<br>Product |
| --- | --- | --- | --- |
| Allyl Alcohol | 380:1 | 74 | 3 |
| Allyl Alcohol | 110:1 | 4$^d$ | 60$^d$ |
| Allyl Alcohol | 110:1 | 40$^e$ | 40$^e$ |
| Allyl Alcohol | 101:1 | 32 | 27 |
| Allyl Alcohol | 111:1 | 44$^c$ | 7$^c$ |
| Allyl Alcohol | 42:1 | 25 | 46 |
| Allyl Cyanide | 250:1 | NA | 0 |
| Allyl Cyanide | 57:1 | NA | 16 |
| Allyl Cyanide | 10:1 | NA | 28 |

$^a$Typical Reaction Conditions: 10 mg [Ru*], 1 mL CH$_2$Cl$_2$, 40° C., 12 h under Ar.
$^b$Determined by $^1$H NMR.
$^c$Reaction not performed under anhydrous conditions.
$^d$1 mL THF, 23° C., 12 h under Ar.
$^e$1 mL THF, 60° C., 12 h under Ar. % Condensation Product Formed and % Propionaldehyde are respectively the molar percent of substrate converted to product and molar percent of substrate converted to by-product. Substrate:Catalyst Ratio is mol:mol.

EXAMPLE 3

Effect of Solvent Choice on Metathesis Condensation

Other experiments were undertaken to further characterize the effect of solvent on Ru*-mediated metathesis condensation of allyl alcohol. The data from some of these experiments showed that coordinating solvents such as THF, dimethoxyethane (DME) and acetone increased the percent of 2-butene-1,4-diol formed in the reaction (not all shown). These experiments also indicated that the subject reaction is highly temperature dependent and that the use of THF as solvent results in a high yield of product. For example, in other experiments using dichloromethane as a solvent, the best yield was 46% substrate conversion using a 42:1 catalyst loading at a temperature of 45° C. In comparison, using THF as the solvent can increase the substrate conversion rate to 60% using a higher substrate:catalyst ratio (110:1) and a milder reaction temperature (23° C.).

EXAMPLE 4

Metathesis Condensation of allyl alcohol

Additional experiments were undertaken to further characterize the Ru*-catalyzed metathesis condensation of allyl alcohol. These experiments were performed according to the protocol described in Example 1. All were performed at 40° C. using 10 mg Ru*. The results of these experiments are summarized below in Table 2. % Metathesis Product=the molar percent of substrate converted to product.

TABLE 2

Condensation of Allyl Alcohol

| Substrate:Catalyst | Reaction Time (h) | % Metathesis Product | Solvent |
|---|---|---|---|
| 380:1 | 5 | 3 | $CH_2Cl_2$ |
| 101:1 | 18 | 27 | $CH_2Cl_2$ |
| 42:1 | 5 | 46 | $CH_2Cl_2$ |
| 111:1 | 12 | 7 | $CH_2Cl_2$ (wet) |
| 60:1 | 24 | trace | $CH_2Cl_2$ (v.wet) |

EXAMPLE 5

Metathesis Condensation of allyl Cyanide

Additional experiments were undertaken to further characterize the Ru*-catalyzed metathesis condensation of allyl cyanide. These experiments were performed according to the protocol described in Example 1. All reactions were performed at 40° C., except the experiment using benzene as solvent was performed at 50° C. The results of these experiments are summarized below in Table 3. % Metathesis Product=the molar percent of substrate converted to product.

TABLE 3

Condensation of Allyl Cyanide

| Substrate (mg) | Catalyst (mg) | Substrate:Catalyst (ratio) | Duration (h) | % Metathesis product | Solvent |
|---|---|---|---|---|---|
| 14 | 64 | 57:1 | 18 | 16 | $CH_2Cl_2$ |
| 20 | 79 | 50:1 | 18 | 27 | $CH_2Cl_2$ |
| 20 | 39 | 25:1 | 18 | 18 | $CH_2Cl_2$ |
| 10 | 8 | 10:1 | 18 | 13 | $CH_2Cl_2$ |
| 10 | 197 | 250:1 | 24 | 0 | $CH_2Cl_2$ |
| 10 | 79 | 100:1 | 18 | trace | $CH_6Cl_6$ |
| 10 | 79 | 100:1 | 18 | 0 | $CH_2Cl_2$ |

OTHER EMBODIMENTS

While the above specification contains many specifics, these should not be construed as limitations on the scope of the invention, but rather as examples of preferred embodiments thereof. Many other variations are possible. For example, it is specifically envisioned that functionalized allylic olefins other than those described in detail above could be condensed via metathesis chemistry according to the methods described above. It is also specifically envisioned that catalysts aside from Ru* could be used to catalyze the reactions described herein. Accordingly, the scope of the invention should be determined not by the embodiments illustrated, but by the appended claims and their legal equivalents.

What is claimed is:

1. A reaction mixture comprising a solvent having dissolved therein both (a) an allyl alcohol substrate and (b) a ruthenium-based catalyst capable of catalyzing the metathesis condensation of the substrate.

2. The reaction mixture of claim 1, wherein the catalyst is 1,3-dimesityl-4,5-dihydroimidazol-2-ylidene ruthenium benzylidene (Ru*).

3. The reaction mixture of claim 1, wherein the solvent is a hydrocarbon-based solvent.

4. The reaction mixture of claim 3, wherein the hydrocarbon-based solvent is selected from the group consisting of dichloromethane, tetrahydrofuran, dimethoxyethane, and acetone.

5. The reaction mixture of claim 1, further comprising an olefin product having a different chemical structure than the substrate, the product being formed by the metathesis condensation of the substrate.

6. The reaction mixture of claim 5, wherein the catalyst is 1,3-dimesityl-4,5-dihydroimidazol-2-ylidene ruthenium benzylidene (Ru*).

7. The reaction mixture of claim 5, wherein the allylic olefin product is 2-butene-1,4-diol.

* * * * *